US011624741B2

(12) United States Patent
Richter et al.

(10) Patent No.: US 11,624,741 B2
(45) Date of Patent: Apr. 11, 2023

(54) SENSOR ARRANGEMENT AND METHOD FOR SENSING AN AMOUNT OR A CONCENTRATION OF A TARGET FLUID IN A MEDIUM WITH THE SENSOR ARRANGEMENT

(71) Applicant: Fraunhofer-Gesellschaft zur Förderung der angewandten Forschung e.V., Munich (DE)

(72) Inventors: Martin Richter, Munich (DE); Lorenz Grünerbel, Munich (DE); Sebastian Kibler, Munich (DE); Agnes Bußmann, Munich (DE); Yuecel Congar, Munich (DE); Henry Leistner, Munich (DE)

(73) Assignee: FRAUNHOFER-GESELLSCHAFT ZUR FÖRDERUNG DER ANGEWANDTEN FORSCHUNG E.V., Munich (DE)

(*) Notice: Subject to any disclaimer, the term of this patent is extended or adjusted under 35 U.S.C. 154(b) by 203 days.

(21) Appl. No.: 17/078,184

(22) Filed: Oct. 23, 2020

(65) Prior Publication Data
US 2021/0382024 A1   Dec. 9, 2021

(30) Foreign Application Priority Data
Jun. 9, 2020 (DE) .......................... 102020207231.0

(51) Int. Cl.
*G01N 33/00* (2006.01)
(52) U.S. Cl.
CPC ....... *G01N 33/0037* (2013.01); *G01N 33/004* (2013.01); *G01N 33/0029* (2013.01); *G01N 33/0039* (2013.01); *G01N 33/0073* (2013.01)

(58) Field of Classification Search
CPC ........... G01N 33/0037; G01N 33/0029; G01N 33/0039; G01N 33/004; G01N 33/0016; Y02A 50/20; G01D 21/02
See application file for complete search history.

(56) References Cited

U.S. PATENT DOCUMENTS

| 6,991,214 B2 | 1/2006 | Richter |
| 10,191,023 B2 | 1/2019 | Bäther et al. |

(Continued)

FOREIGN PATENT DOCUMENTS

| CN | 109174220 A | * | 1/2019 | ............ B01L 3/5027 |
| CN | 210769675 U | * | 6/2020 | ............... F15D 1/02 |

(Continued)

OTHER PUBLICATIONS

German Office Action, dated Feb. 23, 2021, in parallel application No. 10 2020 213 386.7.

*Primary Examiner* — Francis C Gray
(74) *Attorney, Agent, or Firm* — McClure, Qualey & Rodack, LLP

(57) ABSTRACT

According to an embodiment, a sensor arrangement comprises a first micropump, e.g. a microfluidic or peristaltic pump, having a normally closed (NC) safety valve, e.g. at the micropump output, a second micropump, e.g. microfluidic or peristaltic pump, having a normally closed (NC) safety valve, e.g. at the micropump output, and a sensor having a sensor chamber, e.g. a sensor cavity or sensor volume, with a sensor element, e.g. an active sensitive region or layer, in the sensor chamber, wherein the sensor is configured to provide a sensor output signal based on a condition of the fluid, e.g. a gas or liquid, in the sensor chamber. The sensor chamber of the sensor is fluidically coupled between the first and second micropump, and the first and second micropump are configured to provide a defined operation mode of the sensor arrangement based on (Continued)

the respective activation or operation condition of the first and second micropump for providing (1.) a defined negative fluid pressure in the sensor chamber, (2.) a defined positive fluid pressure in the sensor chamber or (3.) a defined fluid flow, e.g. fluid throughput, through the sensor chamber.

29 Claims, 8 Drawing Sheets

(56) References Cited

U.S. PATENT DOCUMENTS

| | | |
|---|---|---|
| 2005/0214863 A1 | 9/2005 | Mcdevitt et al. |
| 2005/0221385 A1* | 10/2005 | Nikiforov .............. G01N 30/88 435/7.1 |
| 2009/0185955 A1* | 7/2009 | Nellissen .......... B01L 3/502738 422/68.1 |
| 2014/0197339 A1* | 7/2014 | Mathies ................ F04B 19/006 251/61.1 |
| 2019/0154554 A1 | 5/2019 | Iwakiri et al. |

FOREIGN PATENT DOCUMENTS

| | | |
|---|---|---|
| DE | 10048376 A1 | 4/2002 |
| WO | 2015104221 A1 | 7/2015 |

* cited by examiner

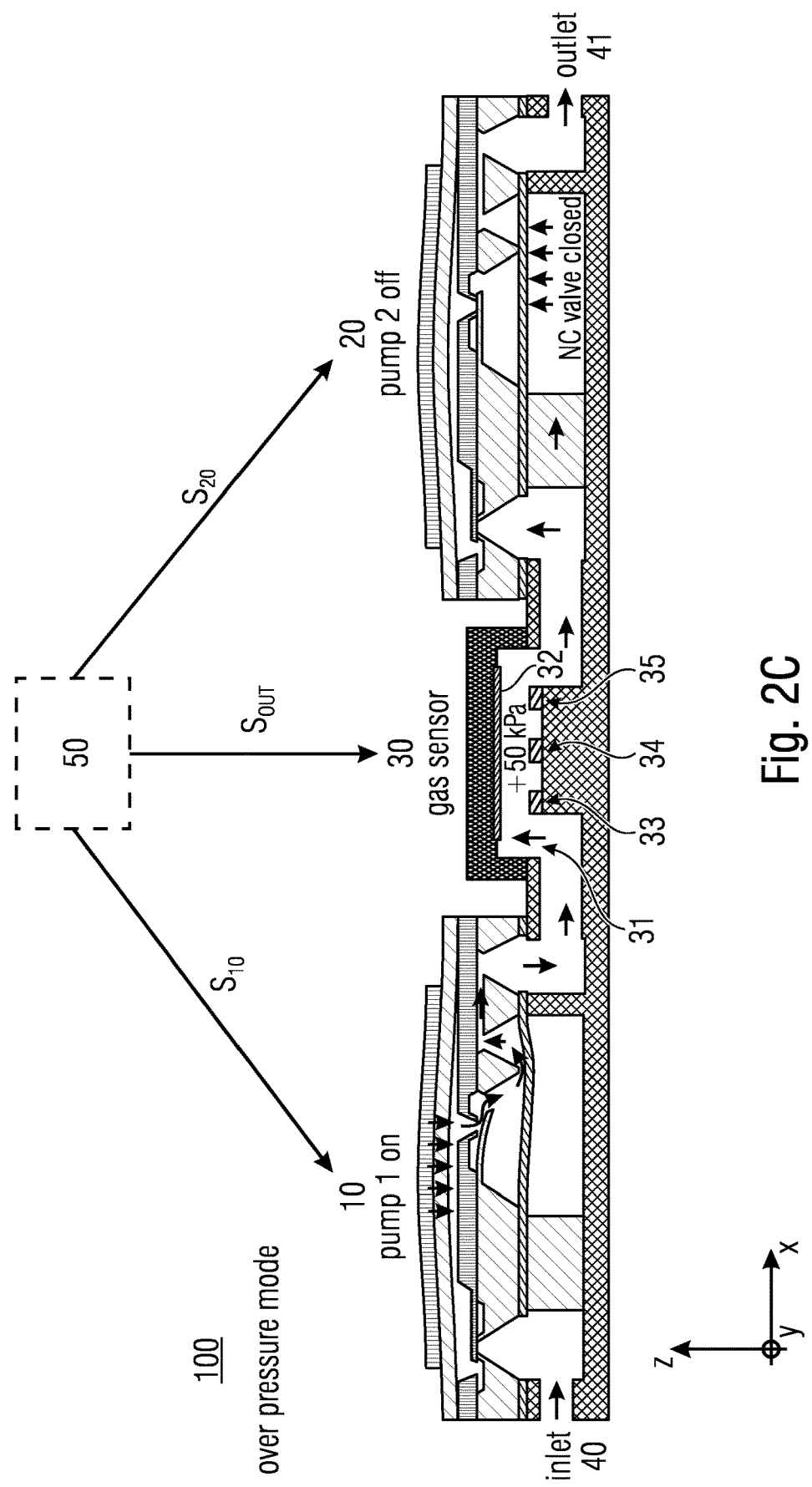

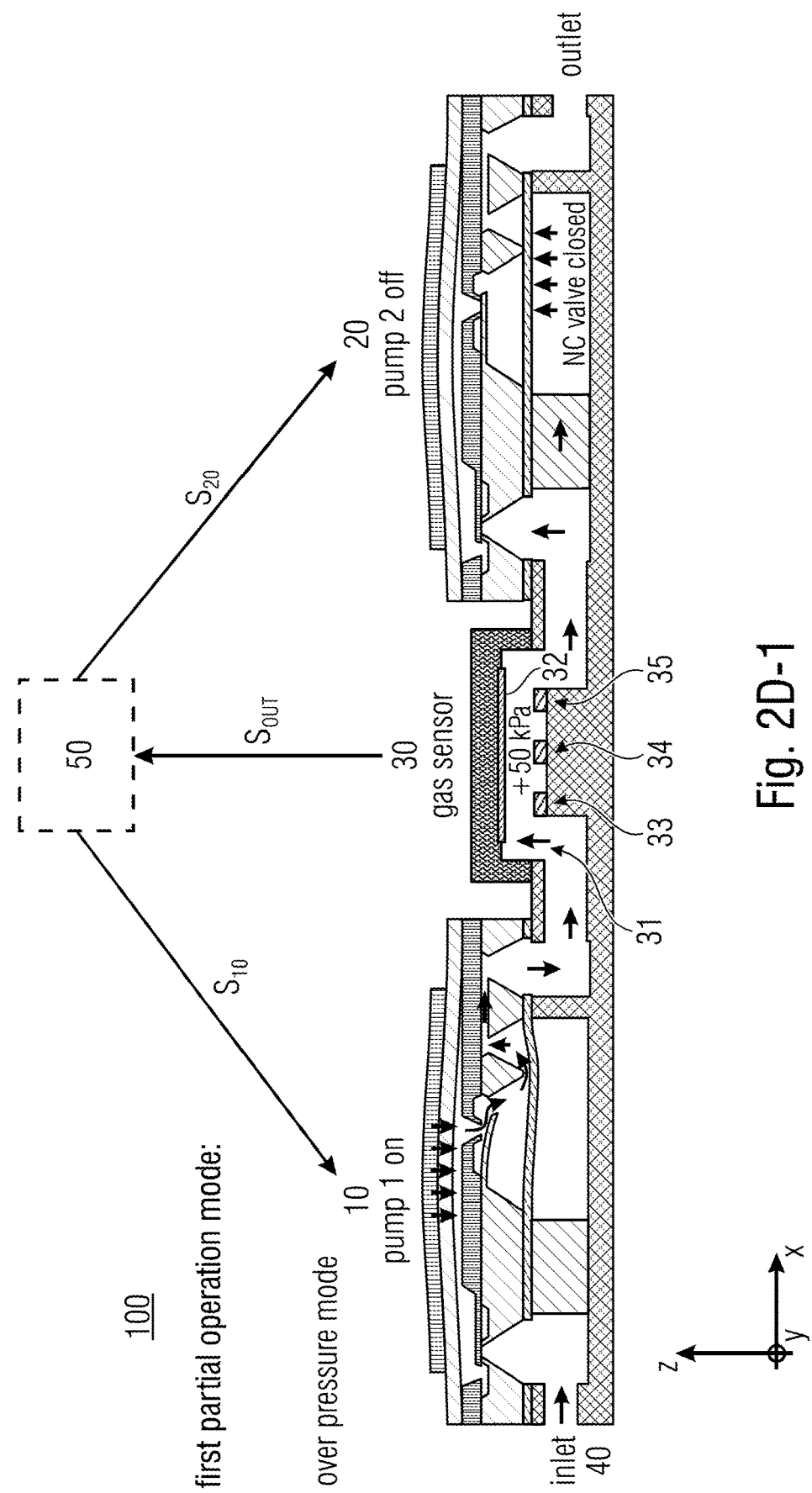

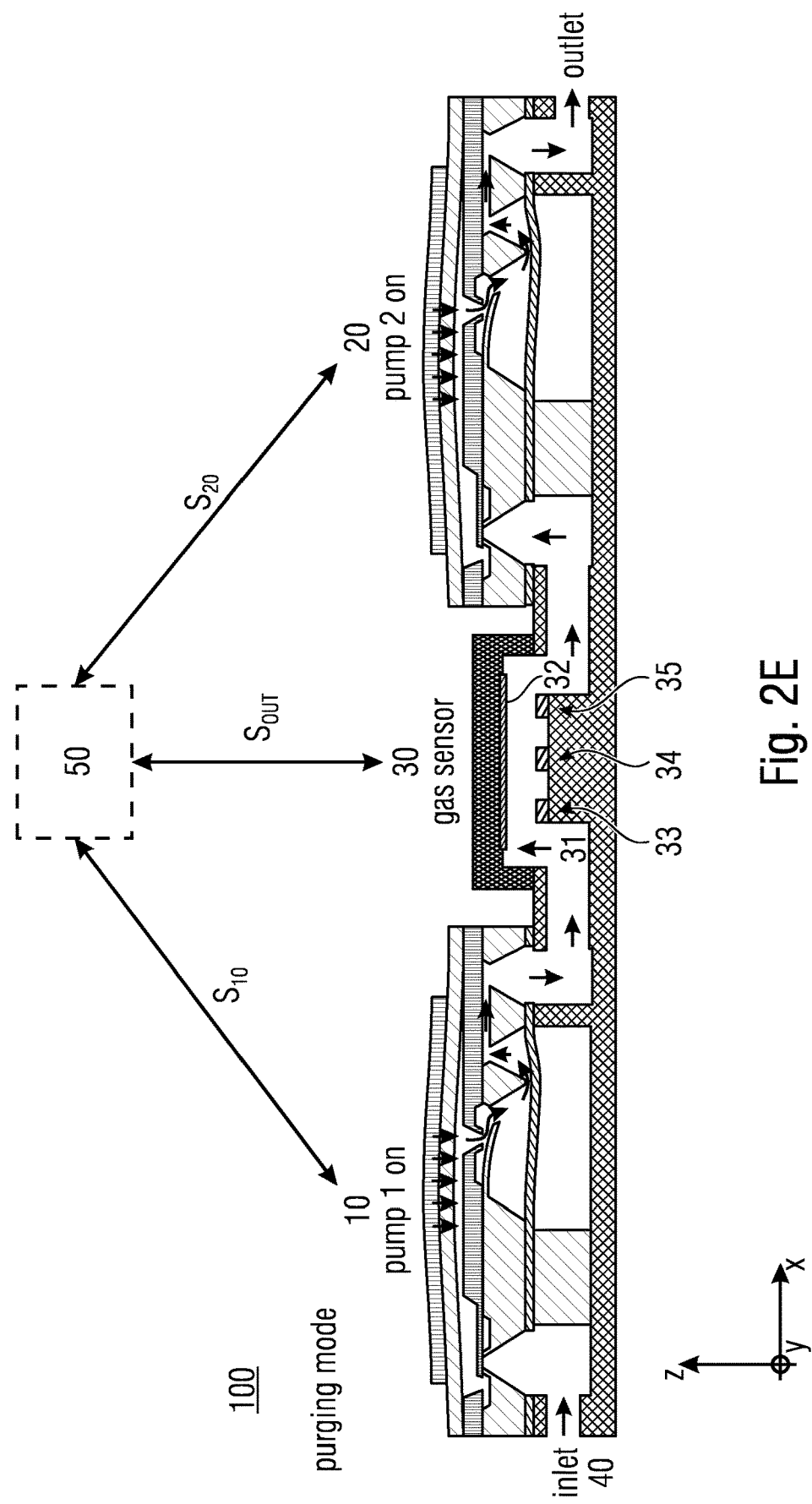

300

| Method for sensing an amount or a concentration of a target fluid in a medium, e.g. a carrier fluid or an environmental medium, with the sensor arrangement according to the preceding claims by: | — 300 |

| Adjusting the operation mode of the first and second micropump, e.g. by means of a processing device, and | — 310 |

| Reading-out the sensor output signal of the sensor in the adjusted operation mode, e.g. by means of the processing device. | — 320 |

Fig. 3

SENSOR ARRANGEMENT AND METHOD FOR SENSING AN AMOUNT OR A CONCENTRATION OF A TARGET FLUID IN A MEDIUM WITH THE SENSOR ARRANGEMENT

TECHNICAL FIELD

Embodiments of the present invention relate to a sensor arrangement and a method for sensing an amount or a concentration of a target fluid in a medium with the sensor arrangement. More specifically, embodiments relate to a micropump with a gas sensor and, in particular, to a fluidic concept using micropumps with a safety valve for a gas sensor.

Gas sensors can detect molecules by an interaction between molecule and a sensitive sensor layer of the gas sensor. The process of adsorption and desorption of different gas molecules with the sensor layer is affecting sensitivity, specificity and drift of the gas sensor. These adsorption and desorption mechanisms can be influenced, e.g., by heating the sensor layer, wherein heating the sensor layer usually increases the desorption of molecules. A pump or micropump can support these processes by transporting the gas molecules to the sensor layer or away from the sensor layer in a defined way.

Reducing the gas pressure in the sensor chamber of the pump or micropump can support the sensor layer regeneration, e.g. the removal (=desorption) of the gas molecules from the sensor layer.

TECHNICAL BACKGROUND

The sensing of environmental parameters in the ambient atmosphere, such as environmental gas components, gains increasingly more importance in the implementation of appropriate sensors which may be used within mobile devices.

For example, WO2015104221 A1 relates to a gas measuring device having a sensor unit for detecting a gas in the sensor unit comprises a pressure-tight measuring channel, a gas inlet for introducing the gas into the measuring channel, a gas outlet for discharging the gas from the measuring channel, and a pump unit for evacuating the measuring channel. The measuring channel has a gas sensor for detecting the gas and a heating unit for heating the gas sensor. The sensor unit can be operated in a measuring mode and a regeneration mode, wherein in the regeneration mode the measuring channel is evacuated and the gas sensor is heated.

Thus, a pump, together with an active valve, generate a negative pressure in the chamber (measuring channel) at the sensor layer to support the gas sensor during a regeneration mode. For that, also a heater is implemented to heat the gas sensor for regeneration. The negative pressure (relative to atmosphere pressure) together with the heating is intended to improve the sensor regeneration.

However, the known prior art has a number of drawbacks and limitations.

Generally, a large dead volume of the gas pump at the sensor chamber has the drawback that a big and powerful pump is needed to generate the desired pressure, e.g. a negative pressure, in a certain time or to generate the higher flowrate to purge the dead volume. Next, active valves move a switching volume when they move the gas.

Therefore, known implementations of a gas sensor comprise a large and bulky arrangement. Such arrangements are difficult to realize in mobile devices. Moreover, such gas sensors have a large dead volume when transporting the gas to and away from the sensor chamber. Moreover, with a pump and an active valve just either negative pressure (pump ahead and valve behind the sensor chamber) or overpressure (pump behind and valve ahead the sensor chamber) can be realized.

Generally, there is a need in the field of gas sensors to provide an improved concept for gas sensors which can be easily integrated in mobile devices.

Such a need can be solved by the sensor arrangement according to claim 1 and the method for sensing an amount or a concentration of a target fluid in a medium according to claim 27.

Further, specific implementations of the sensor arrangement and the method are defined in the dependent claims.

SUMMARY

According to an embodiment, a sensor arrangement comprises a first micropump, e.g. a microfluidic or peristaltic pump, having a normally closed (NC) safety valve, e.g. at the micropump output, a second micropump, e.g. microfluidic or peristaltic pump, having a normally closed (NC) safety valve, e.g. at the micropump output, and a sensor having a sensor chamber, e.g. a sensor cavity or sensor volume, with a sensor element, e.g. an active sensitive region or layer, in the sensor chamber, wherein the sensor is configured to provide a sensor output signal based on a condition of the fluid, e.g. a gas or liquid, in the sensor chamber. The sensor chamber of the sensor is fluidically coupled between the first and second micropump, and the first and second micropump are configured to provide a defined operation mode of the sensor arrangement based on the respective activation or operation condition of the first and second micropump for providing (1) a defined negative fluid pressure in the sensor chamber, (2) a defined positive fluid pressure in the sensor chamber or (3) a defined fluid flow, e.g. fluid throughput, through the sensor chamber.

The present inventive concept for a sensor arrangement and for sensing an amount or a concentration of a target fluid in a medium with the sensor arrangement is based on the finding that the sensor arrangement comprises two micropumps, e.g. two microfluidic or peristaltic pumps, each having a normally closed safety valve, wherein the fluid sensor, e.g. a gas or liquid sensor, is arranged in a sensor chamber which is fluidically coupled between the two micropumps and is apart from that sealed from the environment. As the two micropumps are arranged in a fluidic serial connection and have the same fluidic pumping direction, both, a negative fluid pressure as well as a positive fluid pressure can be generated in the encapsulated sensor chamber.

Based on this implementation of the sensor arrangement a compact solution for the gas sensor can be achieved, wherein the sensor arrangement can realize either negative or positive pressures in the sensor chamber in a small and flat assembly as possible, which also can be easily integrated in mobile devices.

According to a further embodiment, the first micropump comprises a pump inlet, a pump chamber and a pump outlet, wherein the first micropump is configured to pump the fluid, e.g. environmental air, from the pump inlet through the pump chamber to the pump outlet, wherein the second micropump comprises a pump inlet, a pump chamber and a pump outlet, wherein the second micropump is configured to pump the fluid from the pump inlet through the pump chamber to the pump outlet, and wherein the sensor chamber is fluidically coupled between the pump outlet of the first micropump and the pump inlet of the second micropump and is apart from that sealed, e.g. hermetically sealed or encapsulated, from the environment.

Thus, the sensor arrangement comprises a sealed or encapsulated sensor chamber. The encapsulated sensor chamber provides, during measurement, a defined sensor volume, which is encapsulated against the environmental atmosphere outside of the gas sensor. Thus, a disturbing convection may be avoided, if the micropumps are turned off, which results in good conditions for a gas measurement.

According to an embodiment, the first and second micropump, the sensor and the processing device may be integrated to a semiconductor substrate, e.g. a silicon substrate. The integration of the sensor arrangement (or at least substantial portions thereof) in a semiconductor substrate allows to provide a relatively small dead volume of the micropumps in a range of about a few μl (microliter), e.g. in a range between 1 and 10 μl. Based on a relatively small dead volume of the micropumps, the measurement time and measurement accuracy of the fluid sensor can be accelerated (enhanced), wherein, in addition, the calibration of that fluid sensor can be significantly improved. Furthermore, if sharp corners or ridges in the fluid channels of the fluid sensor can be (at least partially) avoided, a dispersion of the fluid or of fluid particles flowing through the fluid sensor can be avoided (minimized) or at least reduced.

According to the first operation mode of the sensor arrangement, a vacuum mode can be implemented in the sensor chamber by means of the first and second micropump. In the first operation mode, the first micropump is in an off-state, e.g. in a turned-off condition or deactivated, and the second micropump is in an on-state, e.g. turned-on condition, activated or energized, for providing the defined negative fluid pressure in the sensor chamber.

The second micropump may be optimized for providing a high negative pressure (relative to atmosphere or environmental pressure). If a high negative pressure is achieved, the sensor arrangement can be calibrated very effectively, e.g. in combination with heating of the fluid sensor element, for example a gas sensing membrane.

According to second operation mode of the sensor arrangement, an overpressure mode can be implemented in the sensor chamber by means of the first and second micropump. In the second operation mode, the first micropump is in an on-state and the second micropump is in an off-state for providing the defined positive fluid pressure in the sensor chamber.

The first micropump may be optimized for providing a high positive pressure. An optional pressure sensor may, for example, measure the pressure in the sensor chamber as a reference value for the sensor readout and as feedback to set a certain pressure in the sensor chamber. Moreover, a high or increased pressure in the sensor chamber may enhance the binding process of the target fluid to the sensor element in the sensor chamber. The integration of a pressure sensor, e.g. a piezo element, in the sensor chamber allows to control the pressure in the sensor chamber and enables to achieve very accurate measurements.

According to a further embodiment, the second operation mode may comprise a first partial operation mode and a subsequent second partial operation mode, wherein, in the first partial operation mode, the first micropump is in an on-state and the second micropump is in an off-state for providing the defined positive fluid pressure in the sensor chamber. In the (immediately) subsequent second partial operation mode, the first micropump is switched in an off-state state and the second micropump is (kept) in the off-state for providing a defined fluid amount, i.e. defined fluid volume or defined measurement volume, in the sensor chamber, e.g. within the fluid path and the sensor chamber. Thus, the sensor element can interact with a defined amount of the "loaded" fluid which is input to the sensor chamber.

According to third operation mode of the sensor arrangement, a purging mode can be implemented in the sensor chamber by means of the first and second micropump. In the third operation mode, the first micropump is in an on-state and the second micropump is in an on-state for providing the defined fluid flow, e.g. with a defined fluid throughput, through the sensor chamber. The purging mode of the sensor arrangement can provide an effective calibration, e.g. again in in combination with heating of the fluid sensor element.

According to a further embodiment, the sensor arrangement may comprise a pressure sensor in the sensor chamber or fluidically coupled to the sensor chamber for measuring a fluid pressure in the sensor chamber.

Generally, if the pressure at the sensor element, e.g. the gas sensor layer, can be adjusted, this feature can be used to get a more specific sensor feedback. To be more specific, a gas measurement at certain pressure levels leads to gas molecule specific binding at the sensor element, hence specific gas measurement is enabled. Thus, providing the pressure sensor allows to change the pressure at sensor element (gas sensor membrane), so that a pressure dependent fluid (gas) absorption profile can be detected.

According to a further embodiment, the first micropump may comprise a plurality of micropump elements in a cascaded arrangement, e.g. fluidically serial connected, for providing an increased positive fluid pressure in the sensor chamber and/or fluidically parallel connected for providing an increased fluid throughput through the sensor chamber.

According to a further embodiment, the second micropump may comprise a plurality of micropump elements in a cascaded arrangement, for providing an increased negative fluid pressure in the sensor chamber and/or an increased fluid throughput through the sensor chamber.

According to a further embodiment, the sensor arrangement may (alternatively or additionally) comprise a heating element in the sensor chamber or thermally coupled to the sensor chamber for heating the fluid, e.g.=adjusting the temperature of the fluid, in the sensor chamber and/or the sensor element of the sensor. Thus, the heating element may provide different measuring temperatures in the sensor chamber. Further, the heating element may provide or at least support a "reset" (regeneration or recovery) of the sensor element, e.g. the active sensor region.

According to a further embodiment, the sensor arrangement may comprise a temperature sensor in the sensor chamber or thermally coupled to the sensor chamber for measuring the temperature in the sensor chamber.

As indicated above, a pressure dependent fluid (gas) absorption profile can be detected, wherein the provision of the temperature sensor and/or heater can provide for a temperature regulation of the fluid in the sensor chamber. Based on a controlled temperature and pressure in the sensor chamber, a temperature/pressure matrix measurement enables to detect specific molecules from that matrix, e.g. by a pattern recognition.

According to a further embodiment, the sensor arrangement may comprise a processing device, e.g. a controller or ASIC, configured to control the operation mode of the first and second micropump, and for reading-out the sensor output signal of the sensor in the set or adjusted operation mode. Thus, the processing device is configured to control the operation mode of a heating element and to read-out a pressure sensor and/or a temperature sensor coupled to the sensor chamber of the sensor.

According to a further embodiment, the processing device may be configured (1.) to control the operation modes of the first and second micropump for adjusting the fluid pressure in the sensor chamber and/or the fluid throughput or fluid flow through the sensor chamber, (2.) to control the heating element for adjusting different or varying temperatures of the fluid and/or the sensor element in the sensor chamber, and (3.) to read-out the sensor output signal at the different temperatures.

According to a further embodiment, the processing device may be further configured to determine a sensor matrix including information (1.) on the read-out sensor output signal, (2.) on the (e.g. different) operation mode(s) of the first and second micropump, and (3.) on the different temperatures in the sensor chamber.

According to a further embodiment, the processing device may be further configured to determine the sensor matrix including information on the measured pressure in the sensor chamber.

According to a further embodiment, the processing device may be further configured to determine the sensor matrix including information on the defined fluid flow, e.g. with a defined fluid throughput, through the sensor chamber.

To summarize, the processing device may set different conditions in the sensor chamber, e.g. one of the different operation modes, the temperature and/or the fluid pressure in the sensor chamber, and may interpret the sensor signal based on the set condition in the sensor chamber. This approach enables to expand the parameter room/space from just temperature T (having a heater) to the parameter pressure P (which can be adjusted) and also Flow rate Q (generated by the micropumps during the set operation mode, e.g. the purge mode, the vacuum mode or the overpressure mode.

Thus, the present sensor concept enables a large number of possibilities to improve the interpretation of the sensor signal regarding sensitivity and specificity.

According to a further embodiment, the processing device may be configured to provide an adjusted actuation having a rectangular or sinusoidal actuation signal to the first and second micropump.

According to a further embodiment, the processing device may be further configured to determine the presence, an amount or a concentration of a target fluid in the fluid in the sensor chamber based on a resulting pressure oscillation profile of the fluid, e.g. having the target fluid, in the sensor chamber.

Moreover, the present sensor concept also allows to use characteristics of the sensor arrangement to interpret the sensor signal regarding sensitivity and specificity.

To be more specific, different time constants for pressurizing (and vacuum building) in the sensor chamber can enhance the effect of specific gas measurement. This can be achieved by slow or fast pumping to fill/empty the sensor chamber.

The same counts for dynamic pressure build up/vacuum building (pressure cycling). Different behavior for varying gas concentrations is expected. However, an adjusted actuation, e.g. a rectangular actuation, can lead to oscillation of the membranes in the system, (even the gas sensing membrane), safety valve membrane or/and molecules, and can negatively affect or impact the sensing process.

According to an embodiment, the sensor element is sensitive for a chemical or physical condition of the fluid in the fluid chamber. The sensor element may sensitive for a concentration of a target fluid or target gas in the fluid in the sensor chamber. The sensor element may sensitive for a presence, an amount and/or a concentration of a target gas in the gas in the sensor chamber, wherein the target gas comprises VOC (VOC=volatile organic compound), $CO_X$, e.g. CO or $CO_2$, $O_X$, e.g. $O_2$ or $O_3$, or $NO_X$, e.g. NO or $NO_2$. The sensor element may be a VOC sensor based on metal oxide, e.g. MOX or metal oxide semiconductor. The sensor element may be an electrochemical sensor having a liquid or solid electrolyte material. Moreover, the sensor element may be sensitive for a concentration of particulate matter in the fluid, e.g. an environmental gas or environmental air, in the sensor chamber.

According to a further embodiment, a method for sensing an amount or a concentration of a target fluid in a medium, e.g. a carrier fluid or an environmental medium, with the above sensor arrangement, the method comprises the steps of adjusting the operation mode of the first and second micropump, e.g. by means of a processing device, and of reading-out the sensor output signal of the sensor in the adjusted operation mode, e.g. by means of the processing device.

According to an embodiment, the method may further comprise the steps of adjusting or changing the temperature of the fluid in the sensor chamber and/or the sensor element of the sensor for providing different measuring temperatures in the sensor chamber, e.g. by means of a heating element which is arranged in the sensor chamber or thermally coupled to the sensor chamber, of measuring the temperature in the sensor chamber, e.g. by means of a temperature sensor in the sensor chamber or thermally coupled to the sensor chamber, and of reading-out the sensor output signal at the different temperatures, e.g. by means of the processing device.

According to an embodiment, the method may further comprise the steps of adjusting the fluid pressure in the sensor chamber and/or the fluid throughput, e.g. the fluid flow, through the sensor chamber, for providing different fluid pressures in the sensor chamber and/or different fluid throughputs, e.g. fluid flows, through the sensor chamber, of measuring the fluid pressure in the sensor chamber and/or the fluid throughput, e.g. the fluid flow, through the sensor chamber, e.g. by means of a pressure sensor, which is arranged in the sensor chamber or fluidically coupled to the sensor chamber, and of reading-out the sensor output signal at the different fluid pressures in the sensor chamber and/or the fluid throughputs through the sensor chamber, e.g. by means of the processing device.

According to an embodiment, the method may further comprise the step of determining, e.g. by means of the processing device, a sensor output signal matrix including information (1.) on the read-out sensor output signal, and (2.) on the operation mode, e.g. on different operation modes, of the first and second micropump.

According to an embodiment, the method may further comprise the step of determining the sensor matrix including information (3.) on the different temperatures in the sensor chamber, e.g. by means of the processing device.

According to an embodiment, the method may further comprise the step of determining the sensor matrix including information (4.) on the measured pressure in the sensor chamber, e.g. by means of the processing device.

According to an embodiment, the method may further comprise the step of determining the sensor matrix including information (5) on the defined fluid flow, e.g. with a defined fluid throughput, through the sensor chamber, e.g. by means of the processing device.

According to an embodiment, the method may further comprise the step of determining, e.g. by means of the processing device, the presence, an amount or a concentration of a target fluid in the fluid in the sensor chamber based on the resulting sensor output signal matrix, wherein the sensor matrix provides a plurality of parameter values, e.g. temperature and/or pressure and/or fluid flow, for each sensor output value.

BRIEF DESCRIPTION OF THE FIGURES

In the following, embodiments of the present disclosure are described in more detail with reference to the figures, in which:

FIGS. 2A-E show different operation modes of the sensor arrangement 100 according to further embodiments; and FIG. 3 shows a schematic block diagram of a method 300 for sensing an amount or a concentration of a target fluid in a medium with the sensor arrangement according to an embodiment.

Figure 1:
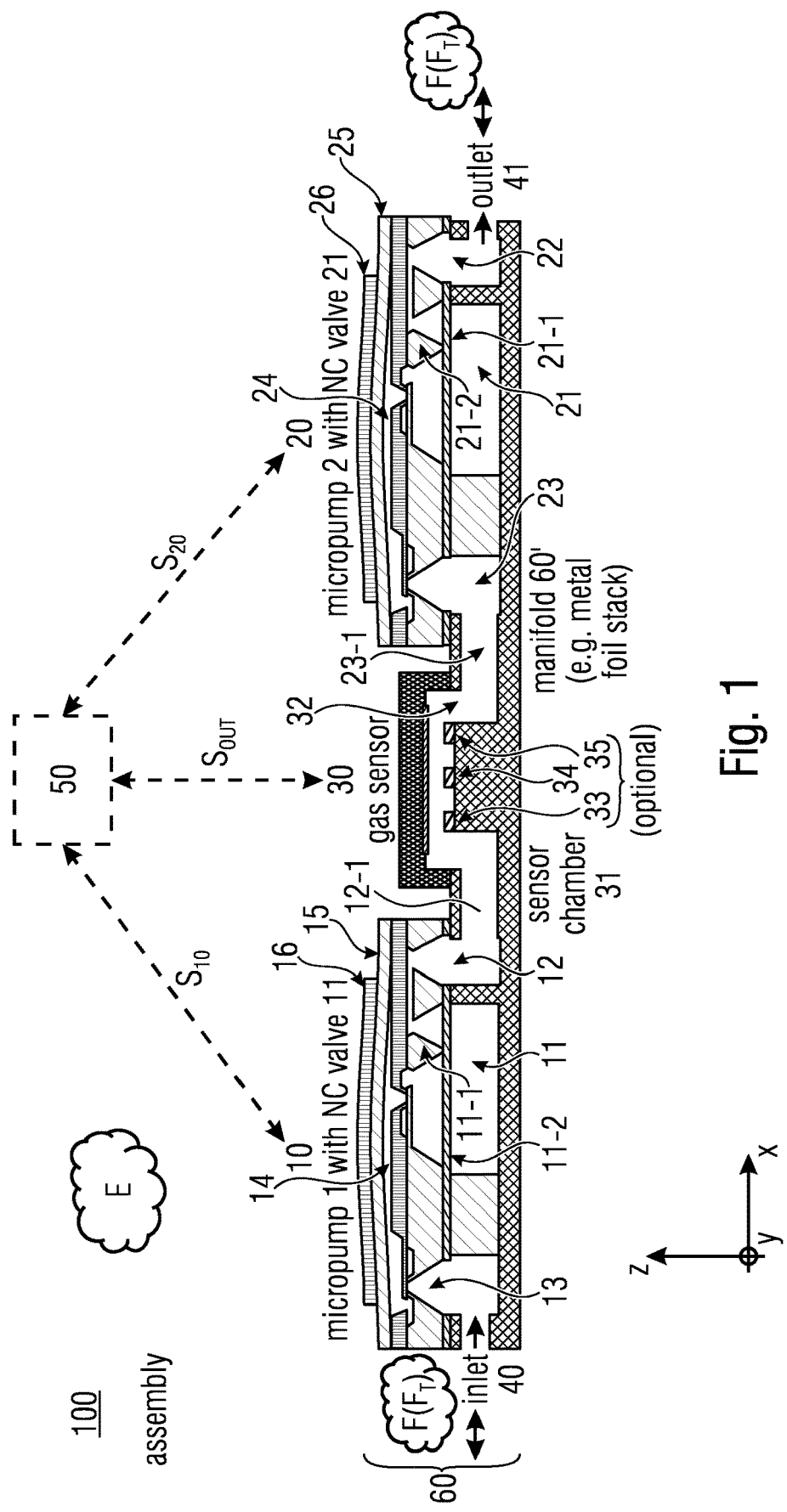
FIG. 1 shows a schematic cross-sectional view of a sensor arrangement 100 according to an embodiment.

In the following description, embodiments are discussed in further detail using the figures, wherein in the figures and the specification identical elements and elements having the same functionality and/or the same technical or physical effect are provided with the same reference numbers or are identified with the same name. Thus, the description of these elements and of the functionality thereof as illustrated in the different embodiments are mutually exchangeable or may be applied to one another in the different embodiments.

DETAILED DESCRIPTION OF THE FIGURES

In the following description, embodiments are discussed in detail, however, it should be appreciated that the embodiments provide many applicable concepts that can be embodied in a wide variety of semiconductor devices. The specific embodiments discussed are merely illustrative of specific ways to make and use the present concept, and do not limit the scope of the embodiments. In the following description of embodiments, the same or similar elements having the same function have associated therewith the same reference signs or the same name, and a description of such elements will not be repeated for every embodiment. Moreover, features of the different embodiments described hereinafter may be combined with each other, unless specifically noted otherwise.

It is understood that when an element is referred to as being "connected" or "coupled" to another element, it may be directly connected or coupled to the other element, or intermediate elements may be present. Conversely, when an element is referred to as being "directly" connected to another element, "connected" or "coupled," there are no intermediate elements. Other terms used to describe the relationship between elements should be construed in a similar fashion (e.g., "between" versus "directly between", "adjacent" versus "directly adjacent", and "on" versus "directly on", etc.).

For facilitating the description of the different embodiments, the figures comprise a Cartesian coordinate system x, y, z, wherein the x-y-plane corresponds, i.e. is parallel, to a first main surface region of a substrate (=a reference plane=x-y-plane), wherein the direction vertically up with respect to the reference plane (x-y-plane) corresponds to the "+z" direction, and wherein the direction vertically down with respect to the reference plane (x-y-plane) corresponds to the "−z" direction. In the following description, the term "lateral" means a direction parallel to the x- and/or y-direction, i.e. parallel to the x-y-plane, wherein the term "vertical" means a direction parallel to the z-direction. In FIGS. 1 and 2A-E, the drawing plane is parallel to the x-z-plane.

FIG. 1 shows a schematic cross-sectional view of a sensor arrangement 100 according to an embodiment, wherein FIGS. 2A-E show different operation modes and conditions of the sensor arrangement 100.

According to an embodiment, the sensor arrangement 100 comprises a first micropump 10, e.g. a microfluidic or peristaltic pump/micropump, which has a normally closed (NC) safety valve 11, e.g. at the micropump output 12 of the first micropump 10. The sensor arrangement 100 further comprises a second micropump 20, e.g. microfluidic or peristaltic pump/micropump, which has a normally closed (NC) safety valve 21 e.g. at the micropump output 22 of the second micropump 20. The sensor arrangement 100 further comprises a sensor 30 having a sensor chamber 31, e.g. a sensor cavity or sensor volume, with a sensor element 32, e.g. an active sensitive region or layer, in the sensor chamber 31, wherein the sensor 30 is configured to provide a sensor output signal based on a condition, e.g. a chemical or physical condition, of the fluid (=gas or liquid) in the sensor chamber 31.

As shown in FIG. 1, the sensor chamber 31 of the sensor 30 is fluidically coupled between the first and second micropump 10, 20. The first and second micropump 10, 20 are configured to provide a defined operation mode of the sensor arrangement 100 based on the respective activation or operation condition of the first and second micropump 10, 20 for providing (1.) a defined negative fluid pressure in the sensor chamber, (2.) a defined positive fluid pressure in the sensor chamber or (3.) a defined fluid flow, e.g. a defined fluid throughput, through the sensor chamber.

According to an embodiment, the first micropump 10 and second micropump 20 are arranged in a fluidic serial connection and have the same fluid pumping direction.

To be more specific, the sensor arrangement 100 comprises two micropumps 10, 20, e.g. two microfluidic or peristaltic pumps, each having a normally closed safety valve 11, 21, wherein the fluid sensor 30, e.g. a gas or liquid sensor, is arranged in a sensor chamber 31 which is fluidically coupled between the two micropumps 10, 20 and is apart from that sealed from the environment E. As the two micropumps 10, 20 are arranged in a fluidic serial connection and have the same fluidic pumping direction, both, a negative fluid pressure as well as a positive fluid pressure can be generated in the encapsulated sensor chamber 31.

According to an embodiment, the sensor arrangement 100 is configured to sense a presence, an amount or a concentration of a target fluid $F_T$ or target fluid component in the fluid F or medium, e.g. a carrier fluid or an environmental medium, in the sensor chamber 31. In the present context, the term fluid may relate to a liquid or a gas. In case, the fluid or medium in the sensor chamber 31 relates to environmental air, the target fluid may relate to a target gas or target gas component which is present in the environmental air (=environmental atmosphere). The present concept is equally applicable to sensing a target liquid or a target liquid component in the environmental medium. In this context, gases and liquids are commonly referred to as fluids.

According to an embodiment, the first micropump 10 comprises a pump inlet 13, a pump chamber 14 and a pump outlet 12, wherein the first micropump 10 is configured to pump the fluid, e.g. environmental air, from the pump inlet 13 through the pump chamber 14 to the pump outlet 12. According to an embodiment, the second micropump 20 comprises a pump inlet 23, a pump chamber 24 and a pump outlet 22, wherein the second micropump 20 is configured to pump the fluid from the pump inlet 23 through the pump chamber 24 to the pump outlet 22. As shown, the sensor chamber 31 is fluidically coupled between the pump outlet 12 of the first micropump 10 and the pump inlet 23 of the second micropump 20 and is apart from that sealed, e.g. hermetically sealed, or encapsulated from the environment.

As shown in the figures, the pump inlet 13 of the first micropump 10 is fluidically coupled or forms the fluid inlet 40 of the sensor arrangement 100, wherein the pump outlet 22 of the second micropump 20 is fluidically coupled or forms the fluid outlet 40 of the sensor arrangement 100. The first and second micropump 10, 20 may be formed as a micro-membrane pump each comprising a passive check valve as the safety valves 11, 21. The micro-membrane pumps 20 may include a pump membrane 15, 25, wherein a piezoceramic element 16, 26 may be attached to the pump membrane 15, 25 such that, by actuating the piezoceramic element 16, 26, a volume of a pump chamber 14, 24 of the diaphragm pumps 10, 20 can be varied. For this purpose, suitable means (e.g. the device 50, see below) are provided for applying a voltage to the piezoceramic element 16, 26 bonded to the pump diaphragm 15, 25 and for deflecting the same from the position as shown in FIG. 1 to a position where the volume of the pump chamber 14, 24 is reduced.

According to an embodiment, the NC safety valve 11 of the first micropump 10 comprises a valve seat 11-1 and a valve lid 11-2 and is arranged at the pump outlet 12 of the first micropump 10, and wherein the NC safety valve 21 of the second micropump 20 comprises a valve seat 21-1 and a valve lid 21-2 and is arranged at the pump outlet 22 of the second micropump 20.

According to an embodiment, the first and second micropump 10, 20, the sensor 30 and, optionally, the processing device 50 (see below) may be integrated to a semiconductor substrate, e.g. a silicon substrate. According to an embodiment, the sensor element 32 is sensitive for a chemical or physical condition of the fluid in the fluid chamber 31. The integration of the sensor arrangement 100 (or at least substantial portions thereof) in a semiconductor substrate 60 allows to provide a relatively small dead volume of the micropumps 10, 20 in a range of about a few µl (microliter), e.g. in a range between 1 and 10 µl. Based on a relatively small dead volume of the micropumps 10, 20, the measurement time and measurement accuracy of the fluid sensor can be accelerated (enhanced), wherein, in addition, the calibration of that fluid sensor 30 can be significantly improved. Furthermore, if sharp corners or ridges in the fluid channels 12-1, 23-1 of the fluid sensor 30 can be (at least partially) avoided, a dispersion of the fluid or of fluid particles F flowing through the fluid sensor 30 can be avoided (minimized) or at least reduced.

Thus, the sensor arrangement 100 comprises a sealed or encapsulated sensor chamber 31. The encapsulated sensor chamber 31 provides, during measurement, a defined sensor volume, which is encapsulated against the environmental atmosphere outside of the gas sensor. Thus, a disturbing convection may be avoided, if the micropumps 10, 20 are turned off, which results in good conditions for a gas measurement.

Based on this implementation of the sensor arrangement 100, a compact solution for the gas sensor can be achieved, wherein the sensor arrangement 100 can realize either negative or positive pressures in the sensor chamber 31 in a small and flat assembly as possible, which also can be easily integrated in mobile devices.

In the following, FIGS. 2A-E show different operation modes and conditions of the sensor arrangement 100 according to further embodiments. According to an embodiment, the sensor arrangement 100 can be operated in different operation modes.

Figure 2A:
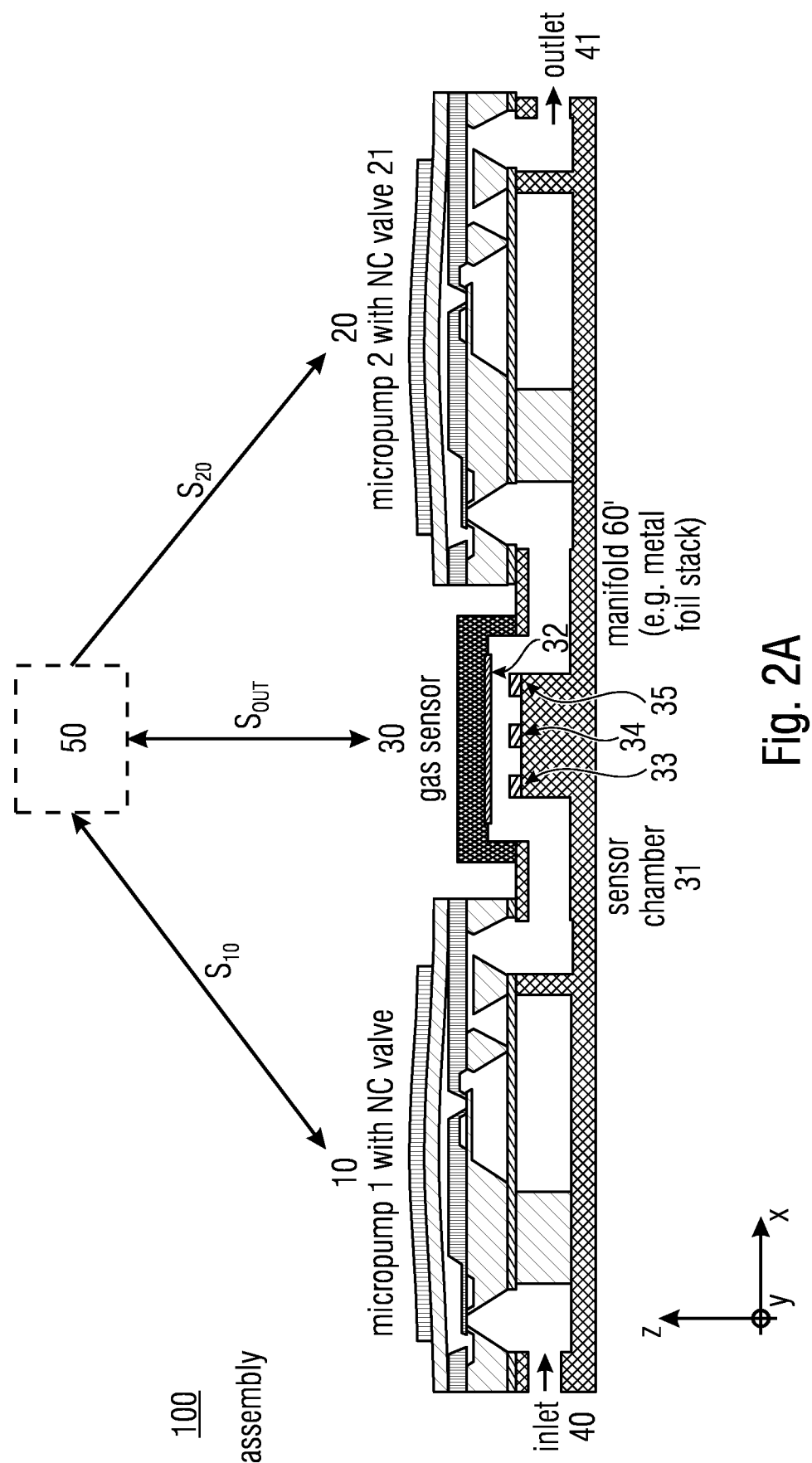

FIG. 2A shows the sensor arrangement 100 in an idle or unoperated condition (see also FIG. 1).

Figure 2B:
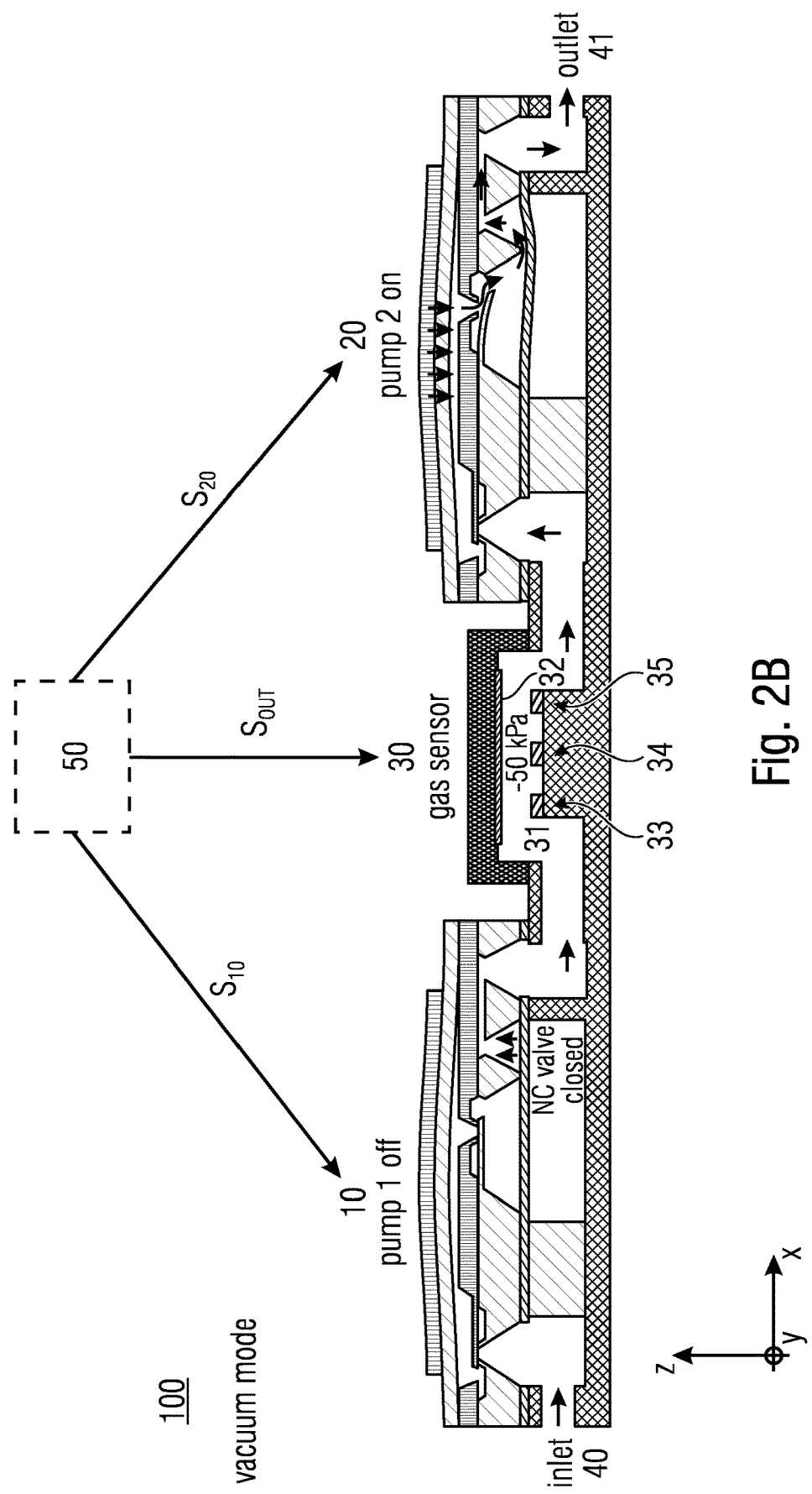

FIG. 2B shows the sensor arrangement 100 in a first operation mode, e.g. a vacuum mode. In the first operation mode (vacuum mode) of the sensor arrangement 100, the first micropump 10 is in an off-state, e.g. in a turned-off condition or deactivated, and the second micropump 20 is in an on-state, e.g. turned-on condition, activated or energized, for providing the defined negative fluid pressure in the sensor chamber 31, as exemplarily shown in FIG. 2B, The second micropump may be optimized for providing a high negative pressure relative to atmosphere pressure (environmental pressure). If a high negative pressure is achieved, the sensor arrangement can be calibrated very effectively, e.g. in combination with heating of the fluid sensor element 32, for example a gas sensing membrane.

According to current technology, the micropumps 10, 20 can achieve, for example, a negative pressure in the range between −40 to −60 kPa (kiloPascal), wherein design adaptations to the micropumps 10, 20 a negative pressure of a single micropump 10, 20 can be increased to about −70 to −80 kPa or even −100 kPa (negative pressure). Thus, the first and second micropumps 10, 20 may be optimized for providing a high negative pressure. An optional pressure sensor 33 may, for example, measure the pressure in the sensor chamber 31 as a reference value for the sensor readout and as feedback to set a certain pressure, e.g., as a set point, in the sensor chamber 31.

FIG. 2C shows the sensor arrangement 100 in a second operation mode, e.g. an over-pressure mode. In the second operation mode (over-pressure mode) the first micropump 10 is in an on-state and the second micropump 20 is in an off-state for providing the defined positive fluid pressure in the sensor chamber 31, as exemplarily shown in FIG. 2C.

The first micropump 10 may be optimized for providing a high positive pressure, e.g. currently the illustrated micropumps 10, 20 can achieve up to 100 kPa air back pressure. An optional pressure sensor 33 may, for example, measure the pressure in the sensor chamber 31 as a reference value for the sensor readout and as feedback to set a certain pressure in the sensor chamber 31. Moreover, a high or increased pressure in the sensor chamber 31 may enhance the binding process of the target fluid $F_T$ to the sensor element 32 in the sensor chamber 31. The integration of a pressure sensor 33, e.g. a piezo element, in the sensor chamber 31 allows to control the pressure in the sensor chamber 31 and enables to achieve very accurate measurements.

Figures 2, 2D:
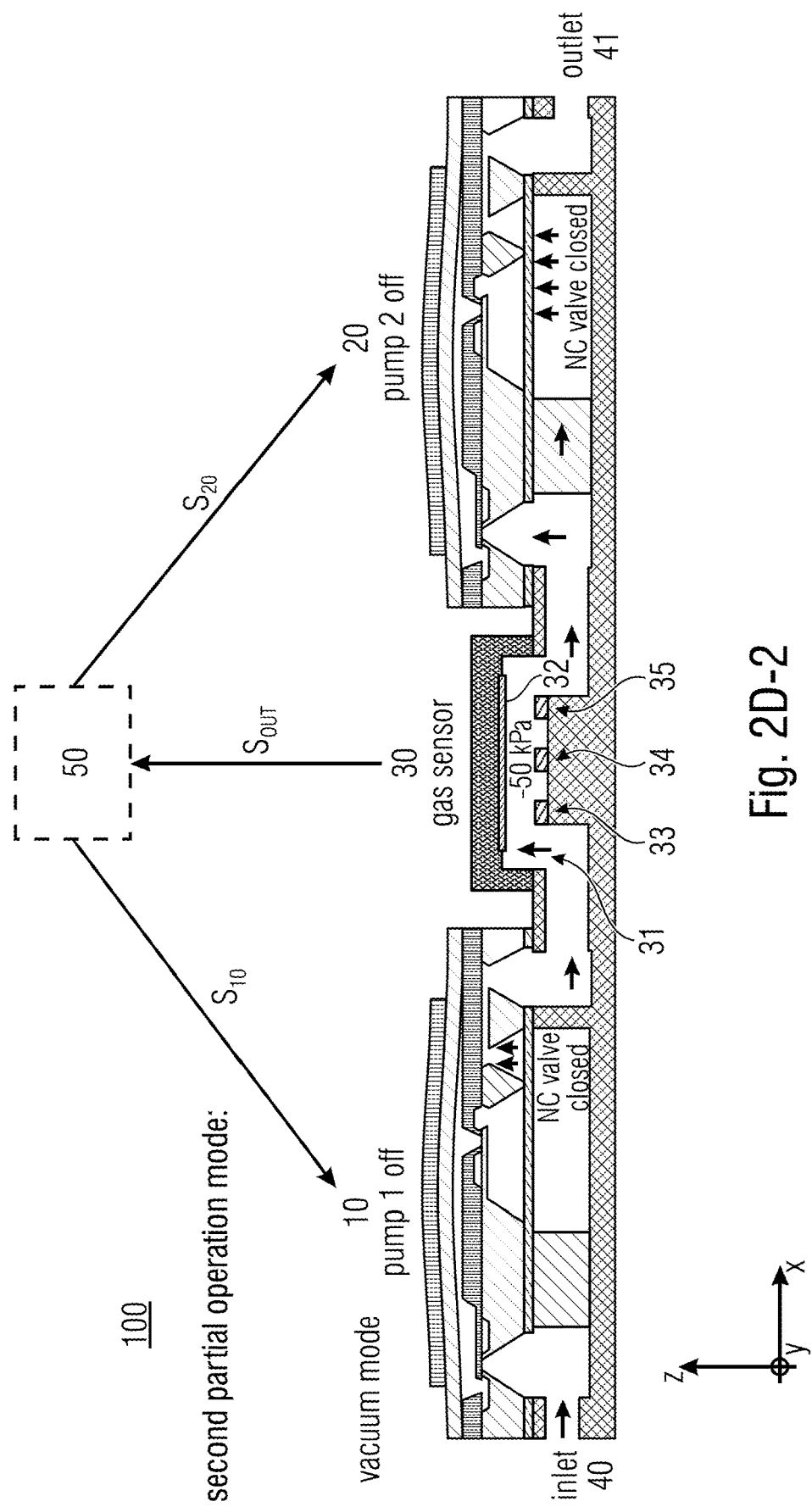

FIG. 2D shows the sensor arrangement 100 in an alternative second operation mode. According to a further embodiment, the second operation mode may comprise a first partial operation mode (as shown in FIG. 2C) and a subsequent second partial operation mode (as shown in FIG. 2D), wherein, in the first partial operation mode, the first micropump 10 is in an on-state and the second micropump 20 is in an off-state for providing the defined positive fluid pressure in the sensor chamber 31. In the (immediately) subsequent second partial operation mode of FIG. 2D, the first micropump 10 is (switched) in an off-state state and the second micropump 20 is (kept) in the off-state for providing a defined fluid amount, i.e. defined fluid volume or defined measurement volume, in the sensor chamber 31, e.g. within the fluid path and the sensor chamber. Thus, the sensor element 32 can interact with a defined amount of the "loaded" fluid F which is input to the sensor chamber 31.

FIG. 2E shows the sensor arrangement 100 in a third operation mode, e.g. a purging mode. In the third operation mode (purging mode) the first micropump 10 is in an on-state and the second micropump 20 is in an on-state for providing the defined fluid flow, e.g. with a defined fluid throughput, through the sensor chamber 31, as exemplarily shown in FIG. 2E.

The purging mode of the sensor arrangement can provide or even enhance an effective calibration, e.g. again in in combination with heating of the fluid sensor element.

According to an embodiment, an energy efficient purge mode could be realized with a 180° phase shift actuation of the micropumps 10, 20 which leads to an improved flowrate of the fluid through the sensor chamber 31.

According to an embodiment, the sensor arrangement 100 may further comprise a pressure sensor 33, which is arranged in the sensor chamber 31 or fluidically coupled to the sensor chamber 31 for measuring a fluid pressure in the sensor chamber 31.

Generally, if the pressure at the sensor element 32, e.g. the gas sensor layer, can be adjusted, this feature can be used to get a more specific sensor feedback. To be more specific, a gas measurement at certain pressure levels leads to gas molecule specific binding at the sensor element 32, hence specific gas measurement is enabled. Thus, providing the pressure sensor 33 allows to change the pressure at sensor element 32 (gas sensor membrane), so that a pressure dependent fluid (gas) absorption profile can be detected.

According to an embodiment, the first micropump 10 may comprise a plurality of micropump elements in a cascaded arrangement, e.g. fluidically serial connected for providing an increased positive fluid pressure in the sensor chamber and/or fluidically parallel connected for providing an increased fluid throughput through the sensor chamber 31.

According to an embodiment, the second micropump 20 may comprise a plurality of micropump elements in a cascaded arrangement, e.g. fluidically serial connected for providing an increased negative fluid pressure in the sensor chamber and/or fluidically parallel connected for providing an increased fluid throughput through the sensor chamber 31.

Thus, cascading the pumps 10, 20 can increase the negative or positive pressure. However, cascading the pumps 10, 20 may require an adapted cap for the pumps 10, 20.

According to an embodiment, the sensor arrangement 100 may further comprise a heating element 34, which is arranged in the sensor chamber 31 or thermally coupled to the sensor chamber 31, for heating the fluid or adjusting the temperature of the fluid in the sensor chamber 31 and/or for heating the sensor element 32 of the sensor 30. Thus, the heating element 34 may provide different measuring temperatures in the sensor chamber 31. Further, the heating element 34 may provide or at least support a "reset" (regeneration or recovery) of the sensor element 32, e.g. the active sensor region.

According to an embodiment, the sensor arrangement 100 may further comprise a temperature sensor 35, which is arranged in the sensor chamber 31 or is thermally coupled to the sensor chamber 31, for measuring the temperature in the sensor chamber 31.

As indicated above, a pressure dependent fluid (gas) absorption profile can be detected, wherein the provision of the temperature sensor 35 and/or heater 34 can provide for a temperature regulation of the fluid F in the sensor chamber 31. Based on a controlled temperature and pressure in the sensor chamber 31, a temperature/pressure matrix measurement enables to detect specific molecules from that matrix, e.g. by a pattern recognition.

Thus, the present sensor arrangement 100 can combine the technical effects of setting and controlling the pressure and temperature of the fluid and/or of the sensor element 32 and the sensor chamber 31 of the sensor 30.

To be more specific, for the interpretation of the sensor output signal $S_{OUT}$ different conditions, e.g., temperature and/or pressure conditions, can be set in the sensor chamber 31, e.g., if the pressure sensor 33, the heater 34 and optionally also the temperature sensor 35 are implemented in the sensor chamber 31.

In case the sensor arrangement 100 is implemented as a VOC gas sensor (VOC=volatile organic compound), it is a challenge to identify specific fluid or fluid compounds, e.g. gases or gas components, of the plurality of different organic compounds. This is especially true, if the sensor arrangement 100 is intended to measure poisonous and/or hazardous gases like formaldehyde or benzene.

Based on the inventive sensor concept, it is possible to interpret the sensor output signal $S_{OUT}$ in different operation conditions which can be set in the sensor chamber 31, so that the present concept enables to expand the parameter space (parameter room) just from temperature T (having the heater 34) to the parameter "pressure p", which can be adjusted by the processing device 50, and also the flow rate Q which can be generated by the micropumps 10, 20 during the purging mode (see for example FIG. 2E).

In the following, some exemplary implementations of the parameter space for interpreting the sensor output signal are described:

A linear field:
Variation of the pressure between p1 ... p2 at a given temperature T.

A matrix (P×T):
Variation of the pressure between p1 ... p2, variation of the temperature between T1, ... T2. The sensor feedback of the entire matrix can be used to recognize a specific gas, so that the specificity of the gas sensor 30 can be improved.

A matrix (Q×T):
Variation of the flowrate between Q1, ... Q2, variation of the temperature between T1, ... T2, the sensor feedback of the entire matrix can be used to recognize a specific gas, so that the specificity of the fluid sensor 30 can be improved.

According to embodiments, the interpretation of this measuring matrix can be supported using machine learning and AI algorithm (AI=artificial intelligence).

According to an embodiment, the sensor arrangement 100 may comprise a processing device 50, e.g. a controller or ASIC, configured to control the operation mode of the first micropump 10 with a first control signal $S_{10}$, to control the operation mode of the second micropump 20 with a second control signal $S_{20}$, and for reading-out the sensor output signal $S_{OUT}$ of the sensor 30 in the set operation mode. Thus, the processing device 50 is configured to control the operation mode of a heating element 34 and to read-out a pressure sensor 33 and/or a temperature sensor 35 coupled to the sensor chamber 31 of the sensor 30.

According to an embodiment, the processing device 50 is configured (1) to control the operation modes of the first and second micropump 10, 20 for adjusting the fluid pressure in the sensor chamber 31 and/or the fluid throughput or fluid flow through the sensor chamber 31, (2) to control the heating element 34 for adjusting different or varying temperatures of the fluid and/or the sensor element in the sensor chamber 31, and (3) to read-out the sensor output signal at the different temperatures.

According to an embodiment, the processing device 50 may be configured to determine a sensor matrix including information (1) on the read-out sensor output signal, (2) on the operation mode, e.g. different operation modes, of the first and second micropump 10, 20, and (3) on the different temperatures in the sensor chamber 31.

According to an embodiment, the processing device 50 may be further configured to determine the sensor matrix including information (4) on the measured pressure in the sensor chamber 31.

According to an embodiment, the processing device 50 may be further configured to determine the sensor matrix including information (5) on the defined fluid flow, e.g. with a defined fluid throughput, through the sensor chamber 31.

To summarize, the processing device may set different conditions in the sensor chamber, e.g. one of the different operation modes, the temperature and/or the fluid pressure in the sensor chamber, and may interpret the sensor signal based on the set condition in the sensor chamber. This approach enables to expand the parameter room/space from just temperature T (having a heater) to the parameter pressure P (which can be adjusted) and also Flow rate Q (generated by the micropumps during the set operation mode, e.g. the purge mode, the vacuum mode or the over-pressure mode.

Thus, the present sensor concept enables a large number of possibilities to improve the interpretation of the sensor signal regarding sensitivity and specificity.

According to an embodiment, the processing device 50 may be further configured to provide an adjusted actuation having a rectangular or sinusoidal actuation signal $S_{10}$, $S_{20}$ to the first and second micropump 10, 20.

According to an embodiment, the processing device 50 may be further configured to determine the presence, an amount or a concentration of a target fluid in the fluid in the sensor chamber 31 based on a resulting pressure oscillation profile of the fluid, e.g. having the target fluid, in the sensor chamber 31.

Moreover, the present sensor concept also allows to use dynamic characteristics of the sensor arrangement to interpret the sensor signal regarding sensitivity and specificity.

To be more specific, different time constants for pressurizing (and vacuum building) in the sensor chamber can enhance the effect of specific gas measurement. This can be achieved by slow or fast pumping to fill/empty the sensor chamber.

The same counts for dynamic pressure build up/vacuum building (pressure cycling). Different behavior for varying gas concentrations is expected. However, an adjusted actuation, e.g. a rectangular actuation, can lead to oscillation of the membranes in the system, (even the gas sensing membrane), safety valve membrane or/and molecules, and can negatively affect or impact the sensing process.

According to an embodiment, the processing device 50 may be further configured to provide an adjusted or set actuation having a rectangular or sinusoidal actuation signal $S_{10}$, $S_{20}$ to the first and/or micropump 10, 20, respectively.

According to an embodiment, the processing device 50 can be configured to provide a rectangular actuation (only) if a high volume flow Q is required for "cleaning" the sensor 30. Then, the processing device 50 can be configured to switch to a harmonic actuation, e.g., a sinusoidal actuation, for a unicast equalization or may be configured to stop the pumping operation during a sensing operation.

According to an embodiment, the processing device 50 may be configured to retrieve or read-out a "pressure oscillation profile" of the fluid or gas F, wherein the pressure oscillation profile is specific for some fluid or gas molecules. This can lead to a different binding behavior of the target fluid and, thus, to a variation of the sensor response (sensor output signal) which can be interpreted by the processing device 50 for retrieving the species (type), amount and/or concentration of the target fluid $F_T$ in the sensor chamber 31. Moreover, an AI analysis (AI=artificial intelligence) and pattern recognition can provide a very specific fluid or gas sensitivity of the sensor 30.

According to the present fluid sensing concept, dynamic influences on the chemical binding process of the target fluid $F_T$ to the sensor element 32, e.g., the sensor membrane, can be observed and interpreted. However, in this connection it is pointed out to the fact that dynamic influences may be difficult to control, since dynamics can easily leave their operation range due to external influences, such as temperature changes, pressure changes, etc.

According to an embodiment, the sensor element 32 is sensitive for a concentration of a target fluid $F_T$ or target gas in the fluid F in the sensor chamber 31. According to an embodiment, the sensor element 32 is sensitive for a presence, an amount and/or a concentration of a target gas in the gas in the sensor chamber 31, wherein the target gas comprises VOC (VOC=volatile organic compound), $CO_X$ (e.g. CO or $CO_2$), $O_X$ (e.g. $O_2$ or $O_3$) or $NO_X$ (e.g. NO or $NO_2$).

According to an embodiment, the sensor element 32 is a VOC sensor based on metal oxide, e.g. a MOX or metal oxide semiconductor. A VOC gas may comprise formaldehyde ($CH_2O$), benzene, hydrogen sulfide ($H_2S$), MTBE, methylene chloride, perchloroethylene, chlorofluorocarbons and chlorocarbons, tetrachloroethene, etc. However, this list of VOC gases to be detected is not to be regarded as exhaustive.

According to an embodiment, the sensor element 32 is an electrochemical sensor having a liquid or solid electrolyte material. According to an embodiment, the sensor element 32 is sensitive for a concentration of particulate matter in the fluid, e.g. an environmental gas or environmental air, in the sensor chamber 31.

According to an embodiment, the safety valve 11, 21, and the valve lids 11-2, 21-2 and, optionally, the valve seats 11-11, 21-1 may be integrated in silicon for providing silicon micropumps 10, 20, or may be formed with metal for providing metal micropumps 10, 20. Alternatively, the valve lids 11-2, 21-2 may be attached as polymer diaphragms and clamped between the respective micropump 10, 20 and the carrier (substrate) 60.

According to an embodiment, the safety valves 11, 21 are integrated to the respective micropump 10, 20, wherein the micropumps 10, 20 can be glued to the carrier 60 and/or manifold 60'. In case of a glue process, a low degassing is recommended for maintaining the operation characteristics of the micropumps 10, 20.

In case, a polymer safety valve diaphragm 11-2, 21-2 is implemented, the micropumps 10, 20 may be clamped to the manifold. Again, a low degassing processing is recommended for the polymer material.

A manifold 60' of the sensor arrangement 100 and/or the sensor 30, respectively, and especially the fluid channels and the sensor chamber 31 of the sensor 30 could be realized by means of metal foils, which may be bonded together by means of a laser welding process.

According to a further embodiment, a direct integration of the manifold 60' of the sensor arrangement 100 in a PCB (PCB=printed circuit board) could be performed, wherein corresponding technologies for fabricating buried vias can be applied to build the respective channels and chambers inside the PCB. In case of a PCB implementation, the only material, which is in contact with the test fluid, is the semiconductor material, e.g. silicon, and the PCB material, e.g. FR4. The PCB material can be covered with a metal, e.g. gold, if necessary, to avoid particle accumulation. This approach enables the usage of MEMS technology (MEMS=microelectromechanical system) and manufacturing processes in combination with MEMS sensors. Metal covered surfaces of the manifold 60' provide a low degassing during manufacturing and usage of the sensor.

According to a further embodiment, the manifold 60' can be realized in a glass material, which also achieves a low fluid (e.g., gas) particle accumulation.

As described above, a pressure sensor 33 may be arranged or integrated in the sensor chamber 31 or may be fluidically coupled to the sensor chamber 31 for measuring a fluid pressure in the sensor chamber 31. Providing a controlled pressure P in the sensor chamber 31 enables to conduct very accurate measurements, wherein a pressure sensor 33 may be realized by means of a piezo resistive pressure sensor, a capacitive pressure sensor, a piezo element, etc.

Moreover, a number of (currently available) pressure sensors 33 have also integrated a temperature sensor 35, which can be used to measure and control the temperature in the sensor chamber 31, based on the heating operation of the heating element 34. The heating element 34 may be integrated in the sensor chamber 31 or may be thermally coupled to the sensor chamber 31 for heating the fluid F in the sensor chamber 31 and/or in the sensor element 32 of the sensor 30.

In the following, some general integration steps for manufacturing the sensor arrangement are now exemplarily described.

According to a first step, both micropumps 10, 20 can be formed from or in the same wafer and may be diced in a single (in one) piece. In step 2, the flow channels 12-1, 23-1 and the gas sensor chamber 31 may be realized already in the chip, e.g., by an etching processing, together with both micropumps 10, 20, wherein, based on semiconductor processing steps, dead volumes of the sensor 30 below 1 µl or below 10 µl can be achieved. In a third step, the fluid sensor technology (e.g. the gas sensor) is integrated into the silicon chip/substrate 60, wherein dead volumes below 0.5 µl can be achieved.

According to an embodiment, a microprocessor ASIC (ASIC=application specific integrated circuit) can be combined with a sensor ASIC for one chip (diced or singulated semiconductor substrate) only, which allows a direct integration into the manifold 60' with the lowest possible energy consumption.

According to an embodiment, the sensor element 32 in the sensor chamber 31 could also be sensitive for a concentration of particulate matter in the fluid F. In this connection it is pointed out to the fact that a fluid sensor or gas sensor 30 could have a cross contamination by particles which could be sensed by an accordingly equipped sensor for sensing particulate matter.

As an adsorption, i.e., the adhesion of atoms, ions or molecules from a fluid (a gas, liquid or dissolved solid) to a surface, as the surface of the sensor element 32, could enhance the chemical reaction and, therefore, the resulting output signal $S_{OUT}$ of the sensor element 32 in an over pressure mode in the sensor chamber can be appropriate for target fluid sensing, i.e. for sensing the presence and/or concentration of the target fluid $F_T$.

According to an embodiment, the sensor arrangement could also be used to implement a micropump desiccator or exsiccator. A desiccator is a seed enclosure containing desiccants used for preserving moisture-sensitive items for another use. A common use for desiccators is to protect chemicals which are hydroscopic or which react with water from humidity.

According to a further embodiment, the sensor arrangement comprising the at least two micropumps 10, 20 may also support and/or provide an appropriate recovery (reset or regeneration) of the sensor element, e.g., the active sensor region, by means of the purging mode as described above.

FIG. 3 shows a schematic block diagram of a method 200 for sensing an amount or a concentration of a target fluid in a medium with the sensor arrangement according to an embodiment.

According to an embodiment, the method 300 for sensing an amount or a concentration of a target fluid in a medium, e.g. a carrier fluid or an environmental medium, with the sensor arrangement 100, as described above, comprises the steps of adjusting the operation mode of the first and second micropump 10, 20, e.g. by means of the processing device 50, and of reading-out the sensor output signal of the sensor 30 in the adjusted operation mode, e.g. by means of the processing device 50.

According to an embodiment, the method 300 may further comprise the steps of adjusting or changing (setting) 330 the temperature of the fluid in the sensor chamber and/or of the sensor element 32 of the sensor 30 for providing different measuring temperatures in the sensor chamber 31, e.g. by means of a heating element 34 which is arranged in the sensor chamber or thermally coupled to the sensor chamber, of measuring 340 the temperature in the sensor chamber 31, e.g. by means of a temperature sensor 35 in the sensor chamber or thermally coupled to the sensor chamber 31, and of reading-out 350 the sensor output signal at the different temperatures, e.g. by means of the processing device 50.

According to an embodiment, the method 300 may further comprise the steps of adjusting 360 the fluid pressure in the sensor chamber 31 and/or the fluid throughput, e.g. the fluid flow, through the sensor chamber 31, for providing different fluid pressures in the sensor chamber 31 and/or different fluid throughputs, e.g. fluid flows, through the sensor chamber 31, of measuring 370 the fluid pressure in the sensor chamber and/or the fluid throughput, e.g. the fluid flow, through the sensor chamber 31, e.g. by means of a pressure sensor 33, which is arranged in the sensor chamber or fluidically coupled to the sensor chamber 31, and of reading-out 380 the sensor output signal at the different fluid pressures in the sensor chamber 31 and/or the fluid throughputs through the sensor chamber 31, e.g. by means of the processing device 50.

According to an embodiment, the method 300 may further comprise the step of determining 390, e.g. by means of the processing device 50, a sensor output signal matrix including information (1) on the read-out sensor output signal, and (2) on the operation mode, e.g. on different operation modes, of the first and second micropump 10, 20.

According to an embodiment, the method 300 may further comprise the step of determining 400 the sensor matrix including information (3) on the different temperatures in the sensor chamber 31, e.g. by means of the processing device 50.

According to an embodiment, the method 300 may further comprise the step of determining 410 the sensor matrix including information (4) on the measured pressure in the sensor chamber 31, e.g. by means of the processing device 50.

According to an embodiment, the method 300 may further comprise the step of determining 430 the sensor matrix including information (5) on the defined fluid flow, e.g. with a defined fluid throughput, through the sensor chamber 31, e.g. by means of the processing device 50.

According to an embodiment, the method 300 may further comprise the step of determining 430, e.g. by means of the processing device, the presence, an amount or a concentration of a target fluid in the fluid in the sensor chamber 31 based on the resulting sensor output signal matrix, wherein the sensor matrix provides a plurality of parameter values, e.g. temperature and/or pressure and/or fluid flow, for each sensor output value.

In case of using the present sensor arrangement 100 as a VOC sensor, it is possible to resolve different VOCs and the concentrations thereof in the fluid or medium (e.g. carrier gas) in the sensor chamber 31, as the determined sensor output signal matrix provides a plurality of parameter values, e.g. temperature and/or pressure and/or fluid flow, for each sensor output value. Thus, on the basis of sensor output signal matrix and the plurality of parameter values for each sensor output value, such as temperature and/or pressure and/or fluid flow, different VOCs and the concentrations thereof can be determined by evaluating the distribution of the different parameter values and sensor output values and/or by the characteristic association of the sensor output values to the different parameter values. Thus, a characteristic sensor signal measurement field for the different VOCs can be derived based on the sensor output signals with the associated measurement parameter (e.g. temperature and/or pressure and/or fluid flow in the fluid chamber).

According to a further embodiment, the micropumps 10, 20 may be manufactured to comprise a very low dead volume, so that the measurement volume in the sensor chamber 31 between both micropumps 10, 20 may be exactly determined. Thus, the present sensor arrangement 100 may be implemented with a target gas consuming or absorbing sensor element 32. Based on that gas sensing concept, the micropumps 10, 20 may convey a defined fluid volume to the sensor chamber 31, wherein the target gas, e.g. all target gas molecules, may be consumed, absorbed or bound to the sensor element 32. Based on the defined measurement volume and the resulting sensor output signal, e.g. triggered by all or essentially all target gas molecules in the sensor chamber 31, the exact target gas concentration in the sensor chamber 31 having a defined measurement volume can be determined.

Additional embodiments and aspects are described which may be used alone or in combination with the features and functionalities described herein.

According to an embodiment, a sensor arrangement 100 comprises a first micropump 10 having a normally closed (NC) safety valve 11, a second micropump 20 having a normally closed (NC) safety valve 21, and a sensor 30 having a sensor chamber 31 with a sensor element 32 in the sensor chamber 31, wherein the sensor 30 is configured to provide a sensor output signal $S_{OUT}$ based on a condition of the fluid F in the sensor chamber 31, wherein the sensor chamber 31 of the sensor 30 is fluidically coupled between the first and second micropump 10, 20, and wherein the first and second micropump 10, 20 are configured to provide a defined operation mode of the sensor arrangement 100 based on the respective activation condition of the first and second micropump 10, 20 for providing (1.) a defined negative fluid pressure in the sensor chamber 31, (2.) a defined positive fluid pressure in the sensor chamber 31 or (3) a defined fluid flow through the sensor chamber 31.

According to an embodiment, the first micropump 10 and second micropump 20 are arranged in a fluidic serial connection and have the same fluid pumping direction.

According to an embodiment, in a first operation mode, the first micropump 10 is in an off-state and the second micropump 20 is in an on-state for providing the defined negative fluid pressure in the sensor chamber 31, wherein in a second operation mode, the first micropump 10 is in an on-state and the second micropump 20 is in an off-state for providing the defined positive fluid pressure in the sensor chamber 31, and/or wherein in a third operation mode, the first micropump 10 is in an on-state and the second micropump 20 is in an on-state for providing the defined fluid flow through the sensor chamber 31.

According to an embodiment, the second operation mode comprises a first partial operation mode and a subsequent second partial operation mode, wherein, in the first partial operation mode, the first micropump 10 is in an on-state and the second micropump 20 is in an off-state for providing the defined positive fluid pressure in the sensor chamber 31, and wherein, in the subsequent second partial operation mode, the first micropump 10 is in an off-state state and the second micropump 20 is in the off-state for providing a defined fluid amount in the sensor chamber 31.

According to an embodiment, the first micropump 10 comprises a pump inlet 13, a pump chamber 14 and a pump outlet 12, wherein the first micropump 10 is configured to pump the fluid F from the pump inlet 13 through the pump chamber 31 to the pump outlet 12, wherein the second micropump 20 comprises a pump inlet 23, a pump chamber 24 and a pump outlet 22, wherein the second micropump 20 is configured to pump the fluid F from the pump inlet 23 through the pump chamber 24 to the pump outlet 22, and wherein the sensor chamber 31 is fluidically coupled between the pump outlet 12 of the first micropump 10 and the pump inlet 23 of the second micropump 20 and is apart from that sealed from the environment E.

According to an embodiment, wherein the NC safety valve 11 of the first micropump 10 comprises a valve seat 11-1 and a valve lid 11-2 and is arranged at the pump outlet 12 of the first micropump 10, and wherein the NC safety valve 21 of the second micropump 20 comprises a valve seat 21-1 and a valve lid 21-2 and is arranged at the pump outlet 22 of the second micropump 20.

According to an embodiment, the sensor arrangement 100 further comprises a pressure sensor 33 in the sensor chamber 31 or fluidically coupled to the sensor chamber 31 for measuring a fluid pressure in the sensor chamber 31.

According to an embodiment, the sensor arrangement 100 further comprises a heating element 34 in the sensor chamber 31 or thermally coupled to the sensor chamber 31 for heating the fluid F in the sensor chamber 31 and/or the sensor element 32 of the sensor 30.

According to an embodiment, the sensor arrangement 100 further comprises a temperature sensor 35 in the sensor chamber 31 or thermally coupled to the sensor chamber 31 for measuring the temperature in the sensor chamber 31.

According to an embodiment, the sensor arrangement 100 further comprises a processing device 50 configured to control the operation mode of the first and second micropump 10, 20, and for reading-out the sensor output signal Satyr of the sensor 30 in the adjusted operation mode.

According to an embodiment, the processing device 50 is configured to control the operation mode of a heating element 34 and to read-out a pressure sensor 33 and/or a temperature sensor 35 coupled to the sensor chamber 31 of the sensor.

According to an embodiment, the first micropump 10 comprises a plurality of micropump elements in a cascaded arrangement, and/or wherein the second micropump 20 comprises a plurality of micropump elements in a cascaded arrangement.

According to an embodiment, the processing device 50 is configured (1.) to control the operation modes of the first and second micropump 10, 20 for adjusting the fluid pressure in the sensor chamber 31 and/or the fluid throughput through the sensor chamber 31, (2.) to control the heating element 34 for adjusting different temperatures in the sensor chamber 31, and (3.) to read-out the sensor output signal at the different temperatures.

According to an embodiment, the processing device 50 is configured to determine a sensor matrix including information (1.) on the read-out sensor output signal $S_{OUT}$, (2.) on the operation mode of the first and second micropump 10, 20, and (3.) on the different temperatures in the sensor chamber 31.

According to an embodiment, the processing device 50 is further configured to determine the sensor matrix including information (4.) on the measured pressure in the sensor chamber 31.

According to an embodiment, the processing device 50 is further configured to determine the sensor matrix including information (5.) on the defined fluid flow through the sensor chamber 31.

According to an embodiment, the processing device 50 is configured to provide an adjusted actuation having a rectangular or sinusoidal actuation signal $S_{10}$, $S_{20}$ to the first and second micropump.

According to an embodiment, the processing device 50 is further configured to determine the presence, an amount or a concentration of a target fluid $F_T$ in the fluid in the sensor chamber 31 based on a resulting pressure oscillation profile of the fluid F in the sensor chamber 31.

According to an embodiment, the first and second micropump 10, 20, the sensor 30 and the processing device 50 are integrated to a semiconductor substrate.

According to an embodiment, the sensor element 32 is sensitive for a chemical or physical condition of the fluid F in the sensor chamber 31.

According to an embodiment, the sensor element 32 is sensitive for a concentration of a target fluid $F_T$ in the fluid in the sensor chamber 31.

According to an embodiment, the sensor element 32 is sensitive for a presence, an amount and/or a concentration of a target gas $F_T$ in the gas in the sensor chamber 31, wherein the target gas comprises a volatile organic compound VOC, $CO_X$, $O_X$ or $NO_X$.

According to an embodiment, the sensor element 32 is a VOC sensor based on metal oxide.

According to an embodiment, the sensor element 32 is an electrochemical sensor having a liquid or solid electrolyte material.

According to an embodiment, the sensor element 32 is sensitive for a concentration of particulate matter in the fluid F in the sensor chamber 31.

According to an embodiment, a method 300 for sensing an amount or a concentration of a target fluid $F_T$ in a medium F with the above sensor arrangement 100 comprises the steps of: adjusting 310 the operation mode of the first and second micropump 10, 20, and reading-out 320 the sensor output signal $S_{OUT}$ of the sensor 30 in the set operation mode.

According to an embodiment, the method 300 further comprises the step of setting 330 the temperature of the fluid F in the sensor chamber 31 and/or the sensor 32 element of the sensor 30 for providing different measuring temperatures in the sensor chamber 31; measuring 340 the temperature in the sensor chamber 31, and reading-out 350 the sensor output signal $S_{OUT}$ at the different temperatures.

According to an embodiment, the method 300 further comprises the steps of adjusting 360 the fluid pressure in the sensor chamber 31 and/or the fluid throughput through the sensor chamber 31 for providing different fluid pressures in the sensor chamber 31 and/or different fluid throughputs through the sensor chamber 31, measuring 370 the fluid pressure in the sensor chamber 31 and/or the fluid throughput through the sensor chamber 31, and reading-out 380 the sensor output signal $S_{OUT}$ at the different fluid pressures in the sensor chamber 31 and/or the fluid throughputs through the sensor chamber 31.

According to an embodiment, the method 300 further comprises the step of determining 390 a sensor output signal matrix including information (1.) on the read-out sensor output signal, and (2.) on the set operation mode of the first and second micropump 10, 20.

According to an embodiment, the method 300 further comprises the step of determining 400 the sensor matrix including information (3.) on the different temperatures in the sensor chamber 31.

According to an embodiment, the method 300, further comprises the step of determining 410 the sensor matrix including information (4.) on the measured pressure in the sensor chamber 31.

According to an embodiment, the method 300 further comprises the step of determining 420 the sensor matrix including information (5.) on the defined fluid flow through the sensor chamber 31.

According to an embodiment, the method further comprises the step of determining 430 the presence, an amount or a concentration of a target fluid $F_T$ in the fluid F in the sensor chamber 31 based on the resulting sensor output signal matrix.

Although some aspects have been described as features in the context of an apparatus it is clear that such a description may also be regarded as a description of corresponding features of a method. Although some aspects have been described as features in the context of a method, it is clear that such a description may also be regarded as a description of corresponding features concerning the functionality of an apparatus.

Depending on certain implementation requirements, embodiments of the processing device 50 can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating)

with a programmable computer system such that the respective method is performed. Therefore, the digital storage medium may be computer readable. Some embodiments comprise a data carrier having electronically readable control signals, which are capable of cooperating with a programmable computer system, such that one of the methods described herein is performed.

Generally, embodiments of the processing device can be implemented as a computer program product with a program code, the program code being operative for performing one of the methods when the computer program product runs on a computer. The program code may for example be stored on a machine readable carrier. Other embodiments comprise the computer program for performing one of the methods described herein, stored on a machine readable carrier. In other words, an embodiment of the method is, therefore, a computer program having a program code for performing one of the methods described herein, when the computer program runs on a computer.

A further embodiment of the methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory. A further embodiment comprises a processing means, for example a computer, or a programmable logic device, configured to or adapted to perform one of the methods described herein. A further embodiment comprises a computer having installed thereon the computer program for performing one of the methods described herein.

In some embodiments, a programmable logic device (for example a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer. The methods described herein may be performed using a hardware apparatus, or using a computer, or using a combination of a hardware apparatus and a computer.

In the foregoing Detailed Description, it can be seen that various features are grouped together in examples for the purpose of streamlining the disclosure. This method of disclosure is not to be interpreted as reflecting an intention that the claimed examples require more features than are expressly recited in each claim. Rather, as the following claims reflect, subject matter may lie in less than all features of a single disclosed example. Thus the following claims are hereby incorporated into the Detailed Description, where each claim may stand on its own as a separate example. While each claim may stand on its own as a separate example, it is to be noted that, although a dependent claim may refer in the claims to a specific combination with one or more other claims, other examples may also include a combination of the dependent claim with the subject matter of each other dependent claim or a combination of each feature with other dependent or independent claims. Such combinations are proposed herein unless it is stated that a specific combination is not intended. Furthermore, it is intended to include also features of a claim to any other independent claim even if this claim is not directly made dependent to the independent claim.

Although specific embodiments have been illustrated and described herein, it will be appreciated by those of ordinary skill in the art that a variety of alternate and/or equivalent implementations may be substituted for the specific embodiments shown and described without departing from the scope of the present embodiments. This application is intended to cover any adaptations or variations of the specific embodiments discussed herein. Therefore, it is intended that the embodiments be limited only by the claims and the equivalents thereof.

The invention claimed is:

1. Sensor arrangement comprising:
   a first micropump having a normally closed (NC) safety valve,
   a second micropump having a normally closed safety valve, wherein the first micropump and second micropump are arranged in a fluidic serial connection and have the same fluid pumping direction, and
   a sensor having a sensor chamber with a sensor element in the sensor chamber, wherein the sensor is configured to provide a sensor output signal based on a condition of the fluid in the sensor chamber,
   wherein the sensor chamber of the sensor is fluidically coupled between the first and second micropump, and
   wherein the first and second micropump are configured to provide a defined operation mode of the sensor arrangement based on the respective activation condition of the first and second micropump for providing (1.) a defined negative fluid pressure in the sensor chamber, (2.) a defined positive fluid pressure in the sensor chamber or (3.) a defined fluid flow through the sensor chamber.

2. The sensor arrangement according to claim 1, wherein in a first operation mode, the first micropump is in an off-state and the second micropump is in an on-state for providing the defined negative fluid pressure in the sensor chamber,
   wherein in a second operation mode, the first micropump is in an on-state and the second micropump is in an off-state for providing the defined positive fluid pressure in the sensor chamber,
   and/or
   wherein in a third operation mode, the first micropump is in an on-state and the second micropump is in an on-state for providing the defined fluid flow through the sensor chamber.

3. The sensor arrangement according to claim 2, wherein the second operation mode comprises a first partial operation mode and a subsequent second partial operation mode, wherein, in the first partial operation mode, the first micropump is in an on-state and the second micropump is in an off-state for providing the defined positive fluid pressure in the sensor chamber, and wherein, in the subsequent second partial operation mode, the first micropump is in an off-state state and the second micropump is in the off-state for providing a defined fluid amount in the sensor chamber.

4. The sensor arrangement according to claim 1, further comprising:
   a pressure sensor in the sensor chamber or fluidically coupled to the sensor chamber for measuring a fluid pressure in the sensor chamber.

5. The sensor arrangement according to claim 1, further comprising:
   a heating element in the sensor chamber or thermally coupled to the sensor chamber for heating the fluid in the sensor chamber and/or the sensor element of the sensor.

6. The sensor arrangement according to claim 1, further comprising:
a temperature sensor in the sensor chamber or thermally coupled to the sensor chamber for measuring the temperature in the sensor chamber.

7. The sensor arrangement according to claim 1, further comprising:
a processing device (50) configured to control the operation mode of the first and second micropump (10, 20), and for reading-out the sensor output signal ($S_{OUT}$) of the sensor (30) in the adjusted operation mode.

8. The sensor arrangement according to claim 7, wherein the processing device is configured to control the operation mode of a heating element and to read-out a pressure sensor and/or a temperature sensor coupled to the sensor chamber of the sensor.

9. The sensor arrangement according to claim 7, wherein the processing device is configured (1.) to control the operation modes of the first and second micropump for adjusting the fluid pressure in the sensor chamber and/or the fluid throughput through the sensor chamber, (2.) to control the heating element for adjusting different temperatures in the sensor chamber, and (3.) to read-out the sensor output signal at the different temperatures.

10. The sensor arrangement according to claim 7, wherein the processing device is configured to determine a sensor matrix including information (1.) on the read-out sensor output signal, (2.) on the operation mode of the first and second micropump, and (3.) on the different temperatures in the sensor chamber.

11. The sensor arrangement according to claim 10, wherein the processing device is further configured to determine the sensor matrix including information (4.) on the measured pressure in the sensor chamber.

12. The sensor arrangement according to claim 10 or 11, wherein the processing device is further configured to determine the sensor matrix including information (5.) on the defined fluid flow through the sensor chamber.

13. The sensor arrangement according to claim 7, wherein the processing device is configured to provide an adjusted actuation having a rectangular or sinusoidal actuation signal to the first and second micropump.

14. The sensor arrangement according to claim 7, wherein the processing device is further configured to determine the presence, an amount or a concentration of a target fluid in the fluid in the sensor chamber based on a resulting pressure oscillation profile of the fluid in the sensor chamber.

15. The sensor arrangement according to claim 1, wherein the sensor element is sensitive for a presence, an amount and/or a concentration of a target gas in the gas in the sensor chamber, wherein the target gas comprises a volatile organic compound (VOC), $CO_X$, $O_X$ or $NO_X$.

16. The sensor arrangement according to claim 1, wherein the sensor element is a VOC sensor based on metal oxide.

17. The sensor arrangement according to claim 1, wherein the sensor element is an electrochemical sensor having a liquid or solid electrolyte material.

18. The sensor arrangement according to claim 1, wherein the sensor element is sensitive for a concentration of particulate matter in the fluid in the sensor chamber.

19. Method for sensing an amount or a concentration of a target fluid in a medium with the sensor arrangement according to claim 1, the method comprising:
adjusting the operation mode of the first and second micropump, and
reading-out the sensor output signal of the sensor in the set operation mode.

20. The method of claim 19, further comprising:
setting the temperature of the fluid in the sensor chamber and/or the sensor element of the sensor for providing different measuring temperatures in the sensor chamber;
measuring the temperature in the sensor chamber, and
reading-out the sensor output signal at the different temperatures.

21. The method of claim 19, further comprising:
adjusting the fluid pressure in the sensor chamber and/or the fluid throughput through the sensor chamber for providing different fluid pressures in the sensor chamber and/or different fluid throughputs through the sensor chamber,
measuring the fluid pressure in the sensor chamber and/or the fluid throughput through the sensor chamber, and
reading-out the sensor output signal at the different fluid pressures in the sensor chamber and/or the fluid throughputs through the sensor chamber.

22. The method of any of claim 19, further comprising:
determining a sensor output signal matrix including information (1.) on the read-out sensor output signal, and (2.) on the set operation mode of the first and second micropump.

23. The method of claim 22, further comprising:
determining the sensor matrix including information (3.) on the different temperatures in the sensor chamber.

24. The method of claim 22, further comprising:
determining the sensor matrix including information (4.) on the measured pressure in the sensor chamber.

25. The method of any of claim 22, further comprising:
determining the sensor matrix including information (5.) on the defined fluid flow through the sensor chamber.

26. The method of claim 22, further comprising:
determining the presence, an amount or a concentration of a target fluid in the fluid in the sensor chamber based on the resulting sensor output signal matrix.

27. The sensor arrangement according to claim 1, wherein a pump inlet of the first micropump is fluidically coupled or forms a fluid inlet of the sensor arrangement, and wherein a pump outlet of the second micropump is fluidically coupled or forms the fluid outlet of the sensor arrangement.

28. The sensor arrangement according to claim 1, wherein the first micropump comprises a pump inlet, a pump chamber and a pump outlet, wherein the first micropump is configured to pump the fluid from the pump inlet through the pump chamber to the pump outlet,
wherein the second micropump comprises a pump inlet, a pump chamber and a pump outlet, wherein the second micropump is configured to pump the fluid from the pump inlet through the pump chamber to the pump outlet, and
wherein the sensor chamber is fluidically coupled between the pump outlet of the first micropump and the pump inlet of the second micropump.

29. The sensor arrangement according to claim 28, wherein the fluid is an environmental gas or environmental air.

* * * * *